US008835497B2

(12) United States Patent
Friesen et al.

(10) Patent No.: US 8,835,497 B2
(45) Date of Patent: *Sep. 16, 2014

(54) COMPOSITIONS FOR IMPROVED OXIDATIVE STATUS IN COMPANION ANIMALS

(75) Inventors: Kim Gene Friesen, Carthage, IN (US); Dennis Edward Jewell, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 275 days.

This patent is subject to a terminal disclaimer.

(21) Appl. No.: 12/785,739

(22) Filed: May 24, 2010

(65) Prior Publication Data

US 2010/0234461 A1 Sep. 16, 2010

Related U.S. Application Data

(63) Continuation of application No. 10/884,733, filed on Jul. 2, 2004.

(60) Provisional application No. 60/485,194, filed on Jul. 7, 2003, provisional application No. 60/608,925, filed on Jul. 3, 2003.

(51) Int. Cl.
*A61K 31/198* (2006.01)

(52) U.S. Cl.
USPC .......................................................... 514/562

(58) Field of Classification Search
None
See application file for complete search history.

(56) References Cited

U.S. PATENT DOCUMENTS

| | | | |
|---|---|---|---|
| 3,952,115 A | 4/1976 | Damico et al. | |
| 4,267,195 A | 5/1981 | Boudreau et al. | |
| 4,267,196 A | 5/1981 | Johnston | |
| 4,927,850 A | 5/1990 | Bayless et al. | |
| 5,053,429 A | 10/1991 | Hirsch et al. | |
| 5,084,482 A | 1/1992 | Hirsch et al. | |
| 5,292,773 A | 3/1994 | Hirsch et al. | |
| 5,430,064 A | 7/1995 | Hirsch et al. | |
| 5,571,523 A | 11/1996 | Lee et al. | |
| 5,883,083 A | 3/1999 | Harless | |
| 6,090,414 A | 7/2000 | Passwater et al. | |
| 6,245,364 B1 | 6/2001 | Jones et al. | |
| 6,245,379 B1 | 6/2001 | Lepine | |
| 6,277,435 B1 | 8/2001 | Lacombe et al. | |
| 6,670,396 B2 | 12/2003 | Serhan et al. | |
| 2001/0043983 A1 | 11/2001 | Hamilton | |
| 2002/0115710 A1 | 8/2002 | Zicker et al. | |
| 2003/0054048 A1 | 3/2003 | Smit et al. | |
| 2003/0060503 A1 | 3/2003 | Hamilton | |
| 2003/0124230 A1 | 7/2003 | Zielinski | |
| 2003/0202992 A1 | 10/2003 | Fuchs et al. | |
| 2005/0014698 A1 | 1/2005 | Friesen et al. | |
| 2005/0079247 A1 | 4/2005 | Slilaty | |
| 2010/0022636 A1 | 1/2010 | Friesen et al. | |

FOREIGN PATENT DOCUMENTS

| | | |
|---|---|---|
| CA | 2285490 A1 | 4/2001 |
| DE | 20104950 U | 8/2001 |
| EP | 0655245 | 5/1995 |
| GB | 1497211 A | 1/1978 |
| GB | 2315674 A | 2/1998 |
| GB | 2385768 A | 9/2003 |
| JP | 58065785 | 4/1983 |
| JP | 5320036 | 12/1998 |
| WO | WO 98/014476 | 4/1998 |
| WO | WO 00/44375 A | 8/2000 |
| WO | WO 02/15719 | 2/2002 |
| WO | WO 02/35943 A2 | 5/2002 |
| WO | WO 02/45525 | 6/2002 |
| WO | WO 03/015695 A | 2/2003 |
| WO | WO 03/037103 A1 | 5/2003 |
| WO | WO 2005/006877 A1 * | 1/2005 |
| WO | WO 2005006877 A1 | 1/2005 |
| ZA | 9605149 A | 1/1997 |

OTHER PUBLICATIONS

Merck, The Merck Veterinary Manual, 8th Edition, Merck & Co., Inc., 1998, pp. 1624-1634.*
Sohal et al., Science, 1996, vol. 273, pp. 59-63.*
Levine et al., PNAS, 1996, vol. 93, pp. 15036-15040.*
Lyons et al. Blood glutathionine synthesis rates in healthy adults receiving a sulfur amino acid free diet, PNAS, 97:5071-5076 (2000).
Merck Veterinary Manual, 8th Edition 1998 (Merck) pp. 1624-1634.
Sohal, et al.. Science (1996) 273: 59-63.
Peachey, et al., "The effect of aging on nutrient digestibility by cats fed tallow-, sunflower oil or olive oil-enriched diets" XP002300922 abstract.
"Cystine", http://www.vitaminstuff.com/amino-acid-cystine.html, pp. 1-3 of 3downloaded Aug. 15, 2007.
AAFCO (2001) pp. 130-131.
Allison et al."Effects of Bioflavonoid dietary supplementon acetaminophen-induced oxidative injury to feline erythrocytes", JAVM, 217: 1157-1161 (2000).

(Continued)

*Primary Examiner* — Savitha Rao
*Assistant Examiner* — Gregg Polansky
(74) *Attorney, Agent, or Firm* — Thomas M. Hunter

(57) ABSTRACT

A food composition that is useful for increasing antioxidant levels in the body is provided having increased levels of sulfur-containing amino acids, such as methionine, cysteine, or mixtures thereof. Methods of using these compositions for increasing antioxidant levels in the body in mammals, especially in companion animals, are also provided.

8 Claims, No Drawings

(56) References Cited

OTHER PUBLICATIONS

Bianjchi, "Synthesis of glutathionine in response to methionine load in control subject and in patientswith cirrhosis", Metabolism, 49:1434-1439 (2000).

Borras et al., Age-related changes in the brain of a dog,: Vet Pathol,36:202-211 (1999).

Brigelius-Flohe, et al. "Vitamin E: function and metabolism," FASEBJ.,13:1145-1155 (1999).

Cummings et al. "The canins as an animal model of human aging and dementia", Neurobiology of Aging, 17:259-268 (1996).

Fettman, et al. "Effects of Dietary Cysteine on blood sulfur amino acid, glutathionine, and malondialdehyde concentrations in cats", Am. J. Vet. Res., 60:328-333 (1999).

Frei B., Molecular and Biological mechanisms of antioxidant action,: FASEB J., 13:963-964 (1999).

Fujimoto, et al., The effects of dietary docosahexaenoate on the learning ability of rats,: Health Effects of Fish and Fish Oils, St. Johns Newfoundland: ARTS Biomedical Publishers and Distrubutors, 275-284 (1989.

Harman et al., "Free radical theory of aging: a hypothesis on pathogens of dementia of the Alzheimer's type", Age, 16:23-30 (1993).

Head et al., "Spatial learning and memory as a function of age in the dog," Behavioral Neuroscience, 109:851-858.

Hennessey, "Effects of a program of human interaction and alterations in diet composition on activity of the hypothalamic-pituitary-adrenal axis in dogs housed in a public animal shelter", JAVMA, vol. 221, No. 1, Jul. 1, 2002.

Hill et al., "Effect of dietary antioxidant supplementation before and after oral acetaminophen challenge in cats", Proceedings of the Joint Nutrition Symposium, Antwerp, Belgium (Aug. 21-25) (2002) pp. 20.

Houpt, KA., Cognitive Dysfunction in geriatric cats,: August J.R.ed, Consulations in Feline Internal Medicine 4th Ed. W.B. Saunders, Philadelphia, PA, 583-591 (2001).

Jones, Evidence for the involvement of docosaheaenoic acid in cholinergic stimulated signal transduction at the synapse, Neurochemical Research, 22:663-670 (1997).

International Search Report for International Application No. PCT/US2004/021929 dated Dec. 16, 2004.

International Search Report for International Application No. PCT/US2004/021930 dated Dec. 16, 2004.

Leveque NW, "Cognitive dysfunction in dogs, cats an Alzheimer's like diseases" J. Am. Vet. Med. Assoc., 212:1351 (1998).

Lovell, et al., Elevated 4-hydroxynonenal in ventricular fluid in Alzheimer's diseases, Neurobiology of Aging, 18:457-461 (1998).

Markesbery, et al., "Four hydroxynonenal, a product of lipid peroxidation, is increased in the brain in Alzheimer's diseases," Neurobiology of Aging, 19:33-36 (1998).

McGahon, "Age-related changes in oxidative mechanisms and LTP are reversed by dietary manipulation," Neurobiology of Aging, 20:643-653 (1999).

McGahon, Age-related changes in synaptic function: analysis of the effect of dietary supplementation with omega-3 fatty acids, :Neuroscience, 94:305-314 (1999).

Milgrim, et al., "Landmark discrimination learning in the dog," Learning & Memory, 6:54-61 (1999).

Mori et al., "Long term consumption of a methionine-supplemented diet increases iron and lipid peroxide levels in rat liver", J. Nutr. ,120:2349-2355 (2000).

Nutrient Requirements of Cats (Revised Ed. 1986), pp. 9,10,13-15 and 42.

Rogers, "A health body, a health mind: long Term impact of diet and mood and cognitive function", Proceedings of the Nutrition Society, 60:135-143 (2001).

Sano, et al., "A controlled trial of selegilene, alpha-tocopherol, or both as treatment for Alzheimer's diseases", New England J. of Medicine, 336:1216-1222 (1997).

Seneviratne, et al., "Effects of methionine of endogenous antioxidants in the heart", Am. J. Physiol, 277:H2124:2128 (1999).

Schoenherr et al., "Nutritional modification of inflammatory diseases," Seminars in Veterinary Medicine and surgery (Small Animal), 12:212-222 (1997).

Teeter et al., "Methionine and Cystine Requirements", Journal of Nutrition, No. 108, 1978, pp. 291-295.

Weaver, et al. Health effects and metabolism of dietary eicosapentaenoic acid,: Prog. Food. Nutr. Sci., 12:111-150 (1998).

Webb, E.C. et al., "Goat Meat Quality," Small Ruminant Research, vol. 60, pp. 153-166, 2005.

Youdim, et al. Essential fatty acids and the brain: possible health implications, Int J. Devl. Neurosciences, 18:383-399 (2000).

Database Biosis 'Online! Biosciences Information Services, Philadelphia, PA, US: Growth Developmant and Aging 1999;63:61-70, 1999; Peachey et al., "The Effect of Ageing on Nutrient Digestibility by Cats Fed Beef Tallow-, Sunflower Oil-or Olive Oil-Enriched Diets."

Dietary References Intakes of Vitamin C, Vitamin E, Selenium, and Carotenoids Food and Nutrition Board Institute of Medicine, Natl' Academy Press, D.C., Apr. 2000, pp. 138-140, 223-232, 292-302, 358-361 and 370-371.

Risman, 1998, "Biologically Active Food Additives: Unknown About Unknown," Moscow, pp. 49-53.

\* cited by examiner

COMPOSITIONS FOR IMPROVED OXIDATIVE STATUS IN COMPANION ANIMALS

CROSS REFERENCE TO RELATED APPLICATIONS

This application is a continuation of U.S. application Ser. No. 10/884,733, filed Jul. 2, 2004, which claims the benefit of U.S. Provisional Application 60/485,194, filed Jul. 7, 2003, and which claims the benefit of U.S. Provisional Application No. 60/608,925, filed Jul. 3, 2003, which is a conversion of Ser. No. 10/613,604, filed Jul. 3, 2003, from a utility application to a provisional application, which applications are hereby incorporated by reference in their entirety.

FIELD

The present invention relates to companion-animal diet compositions and, more particularly, to companion-animal diet compositions and methods for increasing blood antioxidant levels and/or oxygen radical absorptive capacity in companion animals.

BACKGROUND

Oxidative stress can result from either or both of an excess of free radicals and a decrease in antioxidant levels in the body. Many diseases and conditions are thought to be associated with increased oxidative stress. Nevertheless, effective dietary approaches for reducing oxidative stress have not been available.

SUMMARY

Accordingly, the inventors herein have succeeded in discovering that feeding a diet composition comprising a sulfur-containing antioxidant, in particular, a sulfur-containing amino acid, decreases oxidative stress by increasing blood antioxidant levels.

Thus, in various embodiments, the present invention includes a method for increasing blood antioxidant levels in a companion animal. The companion animal can be a young companion animal such as a kitten or a puppy or an adult companion animal such as a cat or a dog. The terms "cat" and "feline" are used interchangeably herein. The method can comprise feeding to the companion animal, in particular, a feline an effective amount of a diet comprising at least one sulfur-containing antioxidant. The sulfur-containing antioxidant can be, in particular, a sulfur-containing amino acid. In various embodiments, the sulfur-containing antioxidant can be a sulfur-containing antioxidant other than lipoic acid. In various embodiments, the feline can be a young feline.

The present invention can also include, in various embodiments, a diet composition suitable for feeding to young companion animals. The diet composition can comprise a sulfur-containing antioxidant and, in particular, a sulfur-containing amino acid, in an amount effective in increasing blood antioxidant levels. The sulfur-containing antioxidant can be a sulfur-containing antioxidant other than lipoic acid.

In various embodiments, the companion animal can be a feline and the feline can be a young feline. In various embodiments, the companion animal can be a dog and, in particular, a puppy.

The sulfur-containing antioxidant can, in various embodiments, include sulfur-containing amino acids including cysteine, methionine, taurine, glutathione, s-adenosyl methionine, n-acetyl cysteine, cystathionine, cysteic acid, cysteine sulfinic acid, cystine, methionine sulfone, methionine sulfoxide, betaine, methyl hydroxy analog of methionine and mixtures thereof or a methyl ester of said sulfur-containing amino acid such as, for example, methionine methyl ester. In particular, for compositions and methods involving cats, the sulfur-containing antioxidant can be methionine at a concentration of, for example, from about 0.8 wt. % to about 1.5 wt. %; cysteine at a concentration of, for example, from about 0.2 wt. % to about 0.7 wt. %; of a mixture of cysteine and methionine at a total concentration of, for example, from about 1.0 wt. % to about 2.2 wt. %. For compositions and methods involving dogs, the sulfur-containing antioxidant can be methionine at a concentration of, for example, from about 0.3 wt. % to about 0.6 wt. %; cysteine at a concentration of, for example, from about 0.15 wt. % to about 0.4 wt. %; of a mixture of cysteine and methionine at a total concentration of, for example, from about 0.45 wt. % to about 1 wt. %.

In various embodiments, an increase in antioxidant levels can be indicated by the measurement of by an increase in blood taurine concentrations, an increase in blood oxygen radical absorptive capacity, an increase in blood vitamin E concentrations or combinations thereof. The increase in antioxidant levels can produce improved cognitive function, decreased brain aging, decreased DNA damage, decreased oxidative stress from exercise, improved immune function, improved management of diabetes, improved management of cardiovascular disease, improved management of gastrointestinal disease, increased growth performance in young animal, increased longevity in adult felines or combinations thereof.

DETAILED DESCRIPTION

The present invention provides compositions and methods for increasing blood antioxidant levels in a companion animal and, in particular, a feline. The compositions and methods can involve a diet comprising at least one sulfur-containing antioxidant and, in particular, a sulfur-containing amino acid at a concentration effective in increasing blood antioxidant levels and/or oxygen radical absorptive capacity in the companion animal.

In various embodiments, the compositions and methods can be used with companion animals such as cats or dogs of any age. Young companion animals such as kittens or puppies can be animals up to about one year of age; adult animals can be cats of an age from about one to about seven years and dogs of an age from about one to about five-seven years, depending upon the breed; and senior animals can be cats or dogs of an age greater than about seven years. In various embodiments, the compositions and methods of the present invention can be used in young companion animals such as kittens or puppies from birth up to about one year of age.

A dietary antioxidant, or precursor thereof, can be defined as "a substance in foods that significantly decreases the adverse effects of reactive species, such as reactive oxygen and nitrogen species, on normal physiological function in humans". (*Dietary Reference Intakes of Vitamin C, Vitamin E, Selenium, and Carotenoids*, Food and Nutrition Board Institute of Medicine, National Academy Press, Washington, D.C., April, 2000, p. 42, said reference being incorporated in its entirety by reference).

Numerous antioxidants can be found in nature and many of such antioxidants are sulfur-containing antioxidants. For example, while not intending to be bound by any theoretical mechanism of action, the sulfur-containing amino acid, methionine, is believed to possess free-radical scavenging activity by virtue of its containing a sulfur which is oxidizable, as well as its having chelating ability. Methionine can also serve as precursor of other antioxidant compounds such as, for example, cysteine. As another example, the sulfur-containing amino acid, cysteine, also contains an oxidizable sulfur and this amino acid can serve as a precursor of the antioxidant glutathione. In a further example of a sulfur-containing antioxidant, the sulfonic amino acid, taurine, is believed to act as an antioxidant by reacting with excess hypochlorite produced in the process of phagocytosis to form N-chlorotaurine. Specific, non-limiting examples of sulfur containing antioxidants include sulfur-containing amino acids including cysteine, methionine, taurine, glutathione, s-adenosyl methionine, n-acetyl cysteine, cystathionine, cysteic acid, cysteine sulfinic acid, cystine, methionine sulfone, methionine sulfoxide, betaine, methyl hydroxy analog of methionine, sulfur containing amino acids in addition to those listed above, methyl esters of amino acids such as methionine methyl ester, and the like including other sulfur-containing substance exhibiting the properties described above.

The sulfur-containing antioxidants or sulfur-containing amino acids of the present invention can be naturally occurring or synthetic substances. In various embodiments, the sulfur-containing antioxidants include antioxidants other than lipoic acid.

Total sulfur-containing antioxidants can be supplied to dogs and cats as sulfur-containing amino acids such as, for example, methionine, cysteine and cystine, betaine, and methyl hydroxy analog of methionine. These amino acids and other amino acids can be provided in the pure form as d- and l-isomers, or can be provided by ingredients rich in sulfur-containing amino acids such as poultry by-product meal, soybean meal, corn gluten meal, and the like. Table 1 provided indicates acceptable levels of methionine, cysteine, and Total Sulfur-containing Amino Acids (TSAA), i.e. the total of the concentrations of methionine and cysteine.

TABLE 1

|      | Canine    | Feline   |
| ---- | --------- | -------- |
| Met  | 0.3-0.6%  | 0.8-1.5% |
| Cys  | 0.15-0.4% | 0.2-0.7% |
| TSAA | 0.45-1%   | 1-2.2%   |

The present invention provides a food composition having increased levels of sulfur-containing antioxidants such as the amino acid methionine, for use in mammals, especially companion animals, and particularly for use in dogs or cats. The addition of sulfur-containing amino acids to a feline or canine food can increase the levels of antioxidants in the body, and can provide enhanced growth in young animals, improved longevity in adult animals, and assist in managing age-related problems in older animals.

The term "wt %" as employed throughout the specification and claims refers to wt % calculated on a dry matter basis.

The above compositions and methods are particularly useful wherein the oxidative status of the companion animal can benefit from increased levels of antioxidants, such as young animals in the growth stage, mature animals in need of antioxidants as a preventative for development of disease states related to oxidative stress, and in aging animals already demonstrating health issues related to oxidative stress, such as decreased cognitive abilities.

The base food composition containing these additional sulfur-containing amino acids may be any nutritionally complete diet typically employed with companion animals, and will be suitable for the animal's dietary needs. Additional nutrients where appropriate, including nutraceutical compounds that provide health benefits, may be added.

Canned or dry food may be employed. Wet cat or dog food generally has a moisture content greater than about 65%. Semi-moist cat or dog food typically has a moisture content between about 20% and about 65% and may include humectants, potassium sorbate, and other ingredients to prevent microbial growth (bacteria and mold). Dry cat or dog food (kibble) generally has a moisture content below about 10% and its processing typically includes extruding, drying and/or baking in heat.

Levels of sulfur-containing amino acids may be measured by suitable means known in the art. The maximum levels of total sulfur-containing amino acids, levels of methionine, and levels of cysteine may be added to the feed up to the toxic levels of said amino acids. Toxic levels of the sulfur-containing amino acids may be defined as levels of the amino acids that result in an overall imbalance of the levels of the other amino acids present. Toxic levels of the sulfur-containing amino acids for dogs and cats are further known in the art. As an example, methionine levels in cat foods are not allowed to exceed 1.5 wt % by the American Association of Feed Controllers.

Sulfur-containing amino acids, such as methionine, cysteine, and mixtures thereof, provided in the present food composition are from about 0.15 to about 2.2 wt %. Suitable representative minimum sulfur-containing amino acids concentrations include about 0.15, about 0.2, about 0.3, about 0.45, about 0.8, about 1, about 1.2, and about 1.4 wt %. Suitable representative maximum sulfur-containing amino acids concentrations include about 0.5, about 0.7, about 1, about 1.5, and about 2.2 wt %. Preferred for the present invention are sulfur-containing amino acid concentrations of from about 0.15 to about 1.5 wt %. Additionally preferred for the practice of the present invention are sulfur-containing amino acid concentrations of from about 0.3 to about 1 wt %. Particularly preferred for the practice of the present invention are sulfur-containing amino acid concentrations of from about 0.3 to about 0.6 wt %.

Methionine can be present in the diet compositions of the present invention at a concentration of at least about 0.15%, at least about 0.3 wt. %, at least about 0.4 wt. %, at least about 0.6 wt. %, at least about 0.8 wt. %, at least about 0.9 wt. %, at least about 1 wt %, at least about 1.1 wt. % up to about 1.5% or greater. Cysteine can be present in the diet compositions of the present invention at concentrations of at least about 0.15 wt. %, at least about 0.2 wt. %, at least about 0.3 wt. %, at least about 0.4 wt. %, at least about 0.5% wt. % up to about 0.7% or greater. The combination of methionine and cysteine can also be present at a total concentration of sulfur amino acids of at least about at least about 0.3 wt. %, at least about 0.45 wt. %, at least about 0.6 wt. %, at least about 0.8 wt. %, at least about 1.0 wt. %, at least about 1.2 wt. %, at least about 1.4 wt. %, at least about 1.5 wt. %, at least about 1.6 wt. %, up to about 2.2 wt. %.

When the term "food" is used, this can refer not only to a food product which typically provides most, if not all, the nutrient value for a companion animal, but may also refer to such items as a snack, treat, supplement, and the like.

The food composition may be provided to any mammal, particularly a companion animal, such as a dog or cat, which is in need of improved levels of antioxidants, thus resulting in improved growth rate, or in assistance with health issues that may result from aging.

The benefit provided by the present composition which includes increased levels of methionine, cysteine, or mixtures thereof, has been observed as provided in the data below in growing kitten as an increase in the rate of weight gain.

Example 1

This example illustrates the effect of a food composition having increased amounts of methionine on growth performance in kittens.

Dietary methionine was increased above NRC (1986) and AAFCO (2001) estimates for growing kittens. The results indicate that methionine levels of 1.2 to 1.5 wt % in canned cat foods improve oxygen radical absorption capacity and vitamin E concentrations in the blood of growing kittens, thus improving antioxidant status in growing kittens.

Dietary methionine was fed to growing kittens at three levels (0.77, 1.14, and 1.50%) to determine the effect of methionine on growth performance and antioxidant activity. Kittens were fed meat based, canned diets for 10 weeks post-weaning. Weekly weight gain was increased (Table 2) in cats fed 1.14 wt % and 1.50 wt % dietary methionine compared to cats fed 0.77 wt % dietary methionine. The greater weekly growth rate resulted in heavier kittens at the end of the 10-week growth trial. The data demonstrate a greater methionine requirement for growth in young kittens than current NRC (1986) estimates. Thus, methionine was a limiting nutrient for growth in meat based canned diets.

Kittens fed a diet containing 1.50 wt % dietary methionine had greater blood taurine concentrations, oxygen radical absorptive capacity (ORAC), and vitamin E concentrations than kittens fed 0.77 wt % methionine at week 5 of the trial (Table 2). Whole blood taurine and serum vitamin E concentrations were greater at week 10 for kittens fed 1.50 wt % dietary methionine compared to kittens fed 0.77 wt % dietary methionine. Oxygen radical absorptive capacity was not increased by dietary methionine at week 10.

The data illustrate a link between dietary methionine and blood ORAC and vitamin E concentrations for kittens immediately following weaning. The increase in serum antioxidant levels (vitamin E) and free radical absorbing capacity (ORAC) in kittens fed greater dietary methionine suggests a positive relationship between dietary methionine and blood antioxidant activity. The response to dietary methionine was greater during the first five weeks of the trial, which were more stressful than the final five weeks of the trial.

NRC (1986) estimates for dietary methionine are 0.45 wt % and AAFCO (2001) estimates are 0.62% for growing kittens. The data provided in Tables 2 and 3 below indicate that the methionine requirement for kittens fed wet pet food is about 1.2 to about 1.5 wt % in order to improve antioxidant status and free radical absorption capacity.

TABLE 2

Effect of methionine supplementation on growth performance of kittens

|  | Dietary Methionine, wt % | | | Contrast (P-value) | | |
| --- | --- | --- | --- | --- | --- | --- |
|  | 0.77 | 1.14 | 1.50 | Linear | Quadratic | CV |
| Weekly gain, g | 95.00 | 107.50 | 122.14 | 0.35 | 0.06 | 21.92 |
| Total gain, g | 950.00 | 1075.00 | 1221.43 | 0.35 | 0.06 | 21.92 |
| Final wt., g | 1518.75 | 1612.50 | 1792.86 | 0.35 | 0.06 | 14.43 |

TABLE 3

Effect of methionine supplementation on blood metabolites

|  | Dietary Methionine, wt % | | | Contrast (P-value) | | |
| --- | --- | --- | --- | --- | --- | --- |
| Metabolite | 0.77 | 1.14 | 1.50 | Linear | Quadratic | CV |
| Week 5 | | | | | | |
| Taurine | 575.63 | 630.00 | 783.71 | 0.02 | 0.02 | 17.38 |
| ORAC | 2521.84 | 2694.51 | 3164.36 | 0.02 | 0.50 | 17.13 |
| Vitamin E | 15.63 | 19.86 | 30.19 | 0.01 | 0.14 | 20.96 |
| Week 10 | | | | | | |
| Taurine | 625.75 | 616.13 | 784.57 | 0.02 | 0.18 | 18.39 |
| ORAC | 2972.53 | 2503.38 | 3013.31 | 0.86 | 0.02 | 15.88 |
| Vitamin E | 20.74 | 24.24 | 25.13 | 0.10 | 0.55 | 20.92 |

What is claimed is:

1. A method for increasing blood antioxidant levels in a feline in need thereof, the method comprising feeding to the feline an effective amount of a diet comprising methionine in an amount of about 1.2 wt % to about 1.5 wt %, and cysteine in an amount of about 0.4 wt % to about 0.7 wt %, wherein the methionine and cysteine are present at an amount effective to provide beneficial blood antioxidant levels related to an increase in a taurine concentration, a vitamin E concentration, and/or a blood oxygen radical absorptive capacity in the feline's blood.

2. The method of claim 1 wherein the feline is a kitten.

3. The method according to claim 1, wherein increasing antioxidant levels provides a benefit selected from the group consisting of improved cognitive function, decreased brain aging, decreased DNA damage, decreased oxidative stress from exercise, improved immune function, improved management of diabetes, improved management of cardiovascular disease, improved management of gastrointestinal disease, increased growth performance in young animal and increased longevity in adult felines.

4. The method of claim 3 wherein increasing antioxidant levels increases growth performance in kittens.

5. A method for decreasing oxidative stress in a feline in need thereof comprising feeding to the feline an effective amount of a diet comprising a mixture of cysteine and methionine in an amount of about 1.6 wt % to about 2.2 wt %, wherein the mixture is present at an amount effective to provide beneficial blood antioxidant levels related to an increase in a taurine concentration, a vitamin E concentration, and/or a blood oxygen radical absorptive capacity in the feline's blood thereby decreasing oxidative stress, wherein said beneficial blood antioxidant levels provide a benefit to the feline selected from the group consisting of improved cognitive function, decreased brain aging, decreased DNA damage, decreased oxidative stress from exercise, improved immune function, improved management of diabetes, improved management of cardiovascular disease, improved management of gastrointestinal disease, increased growth performance in young animal and increased longevity in adult felines, and combinations thereof.

6. The method of claim 1 wherein the beneficial blood antioxidant levels is related to an increase in said taurine concentration.

7. The method of claim 1 wherein the beneficial blood antioxidant levels is related to an increase in said Vitamin E concentration.

8. The method of claim 1 wherein the beneficial blood antioxidant levels is related to an increase in said blood oxygen radical absorptive capacity.

* * * * *